United States Patent
Yun et al.

(10) Patent No.: US 7,485,407 B2
(45) Date of Patent: Feb. 3, 2009

(54) SILOXANE COMPOUND, PHOTORESIST COMPOSITION INCLUDING THE SILOXANE COMPOUND AND METHOD OF FORMING A PATTERN USING THE PHOTORESIST COMPOSITION

(75) Inventors: Hyo-Jin Yun, Anyang-si (KR); Jae-Ho Kim, Yongin-si (KR); Young-Ho Kim, Yongin-si (KR); Boo-Deuk Kim, Suwon-si (KR); Do-Young Kim, Seoul (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 217 days.

(21) Appl. No.: 11/640,172

(22) Filed: Dec. 18, 2006

(65) Prior Publication Data

US 2007/0148590 A1 Jun. 28, 2007

(30) Foreign Application Priority Data

Dec. 23, 2005 (KR) .................... 10-2005-0128553

(51) Int. Cl.
| | |
|---|---|
| G03C 1/73 | (2006.01) |
| G03F 7/20 | (2006.01) |
| G03F 7/30 | (2006.01) |
| G03F 7/36 | (2006.01) |
| C07F 7/21 | (2006.01) |

(52) U.S. Cl. .................... 430/270.1; 430/325; 430/326; 430/330; 430/311; 430/313; 430/914; 430/921; 430/925; 430/945; 430/966; 556/460; 556/462

(58) Field of Classification Search .................. None
See application file for complete search history.

(56) References Cited

U.S. PATENT DOCUMENTS

| 5,702,620 | A | 12/1997 | Ohnishi et al. |
| 6,852,468 | B2 | 2/2005 | Sato |
| 2002/0168581 | A1* | 11/2002 | Takeda et al. ............ 430/270.1 |

FOREIGN PATENT DOCUMENTS

| JP | 2003-177538 | 6/2003 |
| KR | 10-2004-0066720 | 7/2004 |

* cited by examiner

*Primary Examiner*—Sin J. Lee
(74) *Attorney, Agent, or Firm*—Lee & Morse, P.C.

(57) ABSTRACT

Disclosed are a siloxane compound, a photoresist composition using the same, and a method of forming a pattern, wherein the siloxane compound is having a general formula:

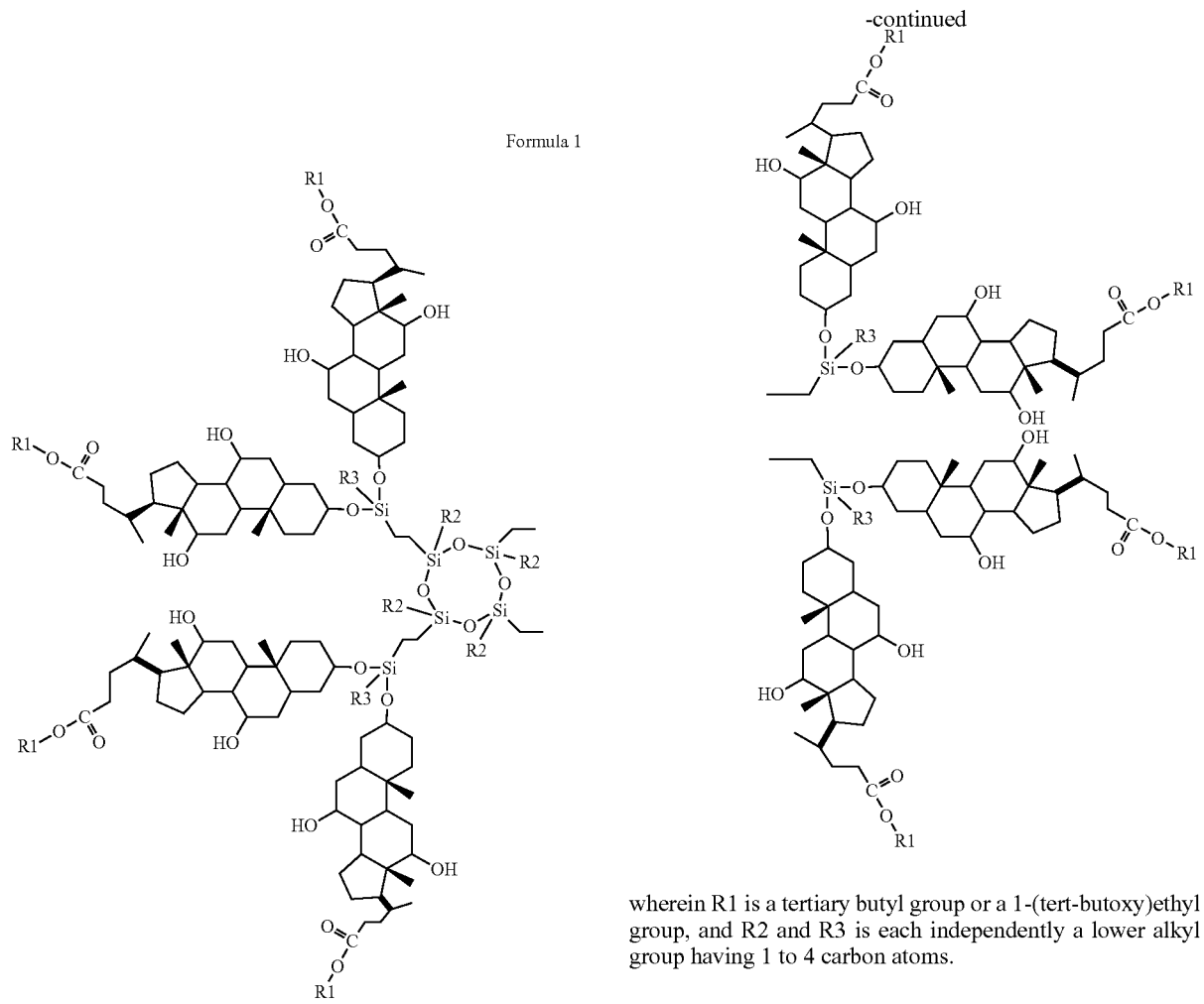
wherein R1 is a tertiary butyl group or a 1-(tert-butoxy)ethyl group, and R2 and R3 is each independently a lower alkyl group having 1 to 4 carbon atoms.
10 Claims, 2 Drawing Sheets

SILOXANE COMPOUND, PHOTORESIST COMPOSITION INCLUDING THE SILOXANE COMPOUND AND METHOD OF FORMING A PATTERN USING THE PHOTORESIST COMPOSITION

BACKGROUND OF THE INVENTION

1. Field of the present invention

The present invention relates to photolithography of semiconductors. More particularly, the present invention relates to a siloxane compound capable of improving an etching resistance of a photoresist pattern during plasma oxygen etching, a photoresist composition including the siloxane compound, and a method of forming a pattern using the same.

2. Description of the Related Art

The rapid development of technologies in the fields of information and communication has triggered enhanced manufacturing growth of computers and semiconductor systems, thereby providing an increased demand for semiconductor devices having high integration density, i.e., semiconductor devices having a reduced size and an enhanced performance in terms of speed and storage capacity. To meet the recent trend in the industry, various semiconductor processing technologies, e.g., photolithography, have been employed to improve the degree of integration, the reliability and the response capability of the semiconductor devices.

The conventional photolithography process may include forming a photoresist pattern that is used as an etching mask and transferring the photoresist pattern onto a surface of a semiconductor substrate via etching. Formation of the photoresist pattern may include preparation of a photoresist composition from a chemically amplified resist (CAR). In particular, the photoresist composition may include a photoacid generator (PAG) for generating an acid material upon light irradiation, a polymer that may chemically react with the generated acid material, and a solvent. For example, the photoresist composition may be deposited on the semiconductor substrate to form a photoresist film and, subsequently, to be selectively irradiated with light. The irradiated portions of the photoresist film may generate an acid material and dissolve, while portions of the photoresist film unexposed to light irradiation may form a photoresist pattern on the semiconductor substrate.

In a conventional photoresist pattern formation, a processing error of about 20 nm may be allowable at each side portion of a photoresist pattern, i.e., total processing error of a line width of 40 nm, of a semiconductor device having a line width of about 240 nm. The processing error of the line width of the photoresist pattern may generate a non-uniform line width, i.e., pattern roughness, having rough side surfaces. For example, a photoresist pattern of a 240 nm semiconductor device having a 20 nm processing error may have a pattern roughness of about 8.3%, i.e., 20/240.

However, as the degree of high-integration increases, the line width of the semiconductor device may decrease and, thereby, increase the pattern roughness thereof. For example, a processing error of about 20 nm in a 90 nm semiconductor may trigger a pattern roughness of about 22%. Similarly, a processing error of about 20 nm in a 70 nm semiconductor may trigger a pattern roughness of about 29%.

Accordingly, attempts have been made to form a photoresist composition capable of reducing the pattern roughness of a semiconductor device. For example, a molecular weight or a blocking group of the polymer employed in the conventional photoresist composition may be modified to improve the pattern roughness thereof. However, such polymer modification may alter the physical characteristics thereof, e.g., size, and, thereby, weaken the photoresist composition.

In another attempt to improve the pattern roughness of the conventional photoresist composition, a uni-molecular material, i.e., a material having a uniform molecular structure and weight, instead of a polymer, has been provided in order to increase the solubility and, thereby, uniformity of the conventional photoresist composition. However, use of such unimolecular material in the conventional photoresist composition may provide an etching resistance that is lower than that of the polymer photoresist, i.e., a photoresist composition having a polymer, thereby providing a weak etching mask during etching.

Accordingly, there exists a need for a photoresist composition capable of providing a low pattern roughness and of exhibiting a high etching resistance.

SUMMARY OF THE INVENTION

The present invention is therefore directed to a siloxane compound, a photoresist composition including the siloxane compound, and a method of forming a photoresist pattern using the same, which substantially overcome one or more of the problems due to the limitations and disadvantages of the related art.

It is therefore a feature of an embodiment of the present invention to provide a siloxane compound capable of increasing an etching resistance of a photoresist pattern employing the same.

It is therefore another feature of an embodiment of the present invention to provide a photoresist composition having a siloxane compound capable of reducing pattern roughness and enhancing etching resistance.

It is yet another feature of an embodiment of the present invention to provide a method of forming a photoresist pattern having reduced pattern roughness and enhanced etching resistance with a photoresist composition having a siloxane compound.

At least one of the above and other features and advantages of the present invention may be realized by providing a siloxane compound represented by Formula (1):

Formula 1

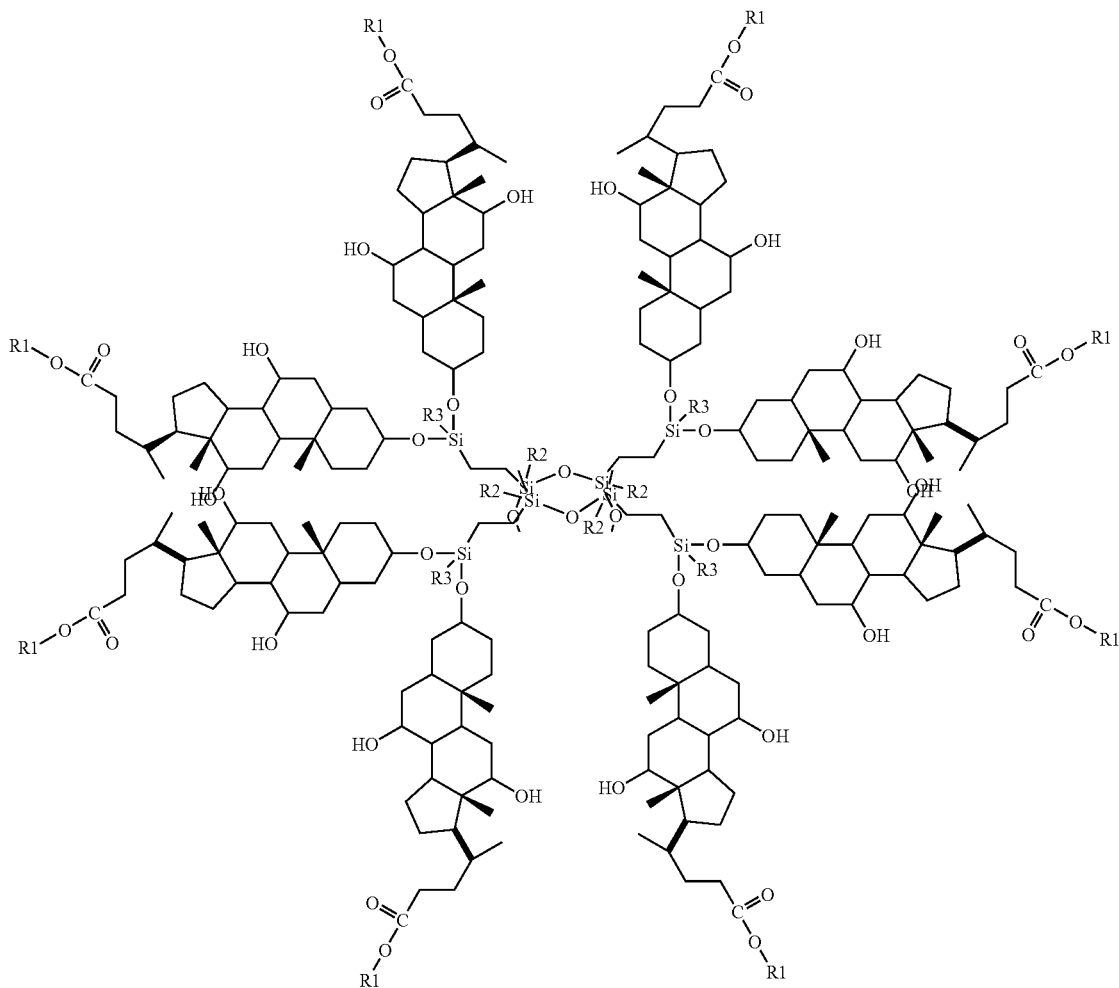

wherein R1 is a tertiary butyl group or a 1-(tert-butoxy)ethyl group, and each of R2 and R3 is, independently, a lower alkyl group having 1 to 4 carbon atoms. The siloxane compound may be a product of a chemical reaction between a first reactant represented by Formula (2) and a second reactant represented by Formula (3):

Formula 2

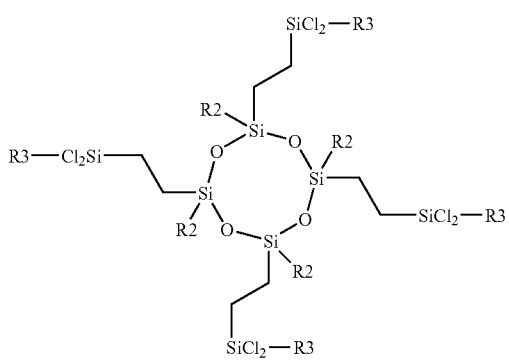

-continued

Formula 3

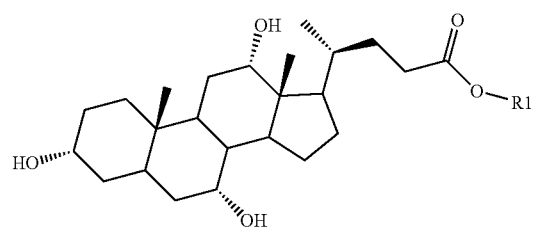

In another aspect of the present invention, there is provided a photoresist composition including a siloxane compound in an amount of about 8 to about 14 percent by weight of the photoresist composition, a photoacid generator in an amount of about 0.1 to about 0.5 percent by weight of the photoresist composition, and an organic solvent, wherein the siloxane compound is represented by Formula (1):

Formula 1

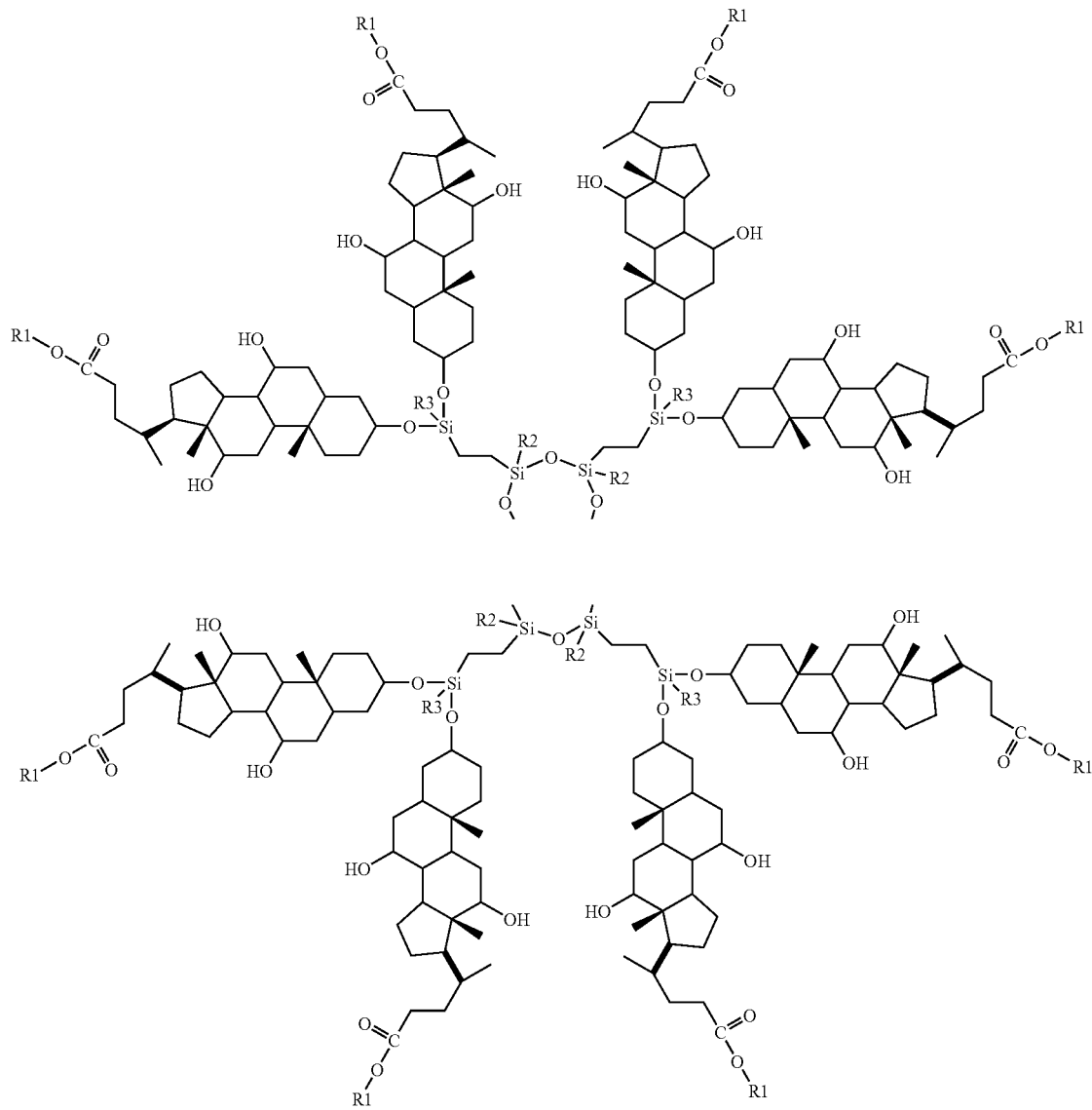

wherein R1 is a tertiary butyl group or a 1-(tert-butoxy)ethyl group, and each of R2 and R3 is, independently, a lower alkyl group having 1 to 4 carbon atoms.

The photoacid generator may be triarylsulfonium salt, diaryliodonium salt, sulfonate, N-hydroxysuccinimide triflate or a combination thereof. The organic solvent may be ethylene glycol monomethyl ether, ethylene glycol monoethyl ether, propylene glycol methyl ether, methyl cellosolve acetate, ethyl cellosolve acetate, diethylene glycol monomethyl ether, diethylene glycol monoethyl ether, propylene glycol methyl ether acetate, propylene glycol propylether acetate, diethylene glycol dimethylether, ethyl lactate, toluene, xylene, methyl ethyl ketone, cyclohexanone, 2-heptanone, 3-heptanone, 4-heptanone or a combination thereof.

In yet another aspect of the present invention, there is provided a method of forming a photoresist pattern on a substrate, including coating the substrate with a mask layer, preparing a photoresist composition having about 8 to about 14 percent by weight of a siloxane compound, about 0.1 to about 0.5 percent by weight of a photoacid generator, and an organic solvent; applying the photoresist composition to the mask layer to form a photoresist film; partially exposing the photoresist film to a light; developing the photoresist film into photoresist pattern; and etching the mask layer through the photoresist pattern form a pattern on the substrate, wherein the siloxane compound is represented by Formula (1):

Formula 1

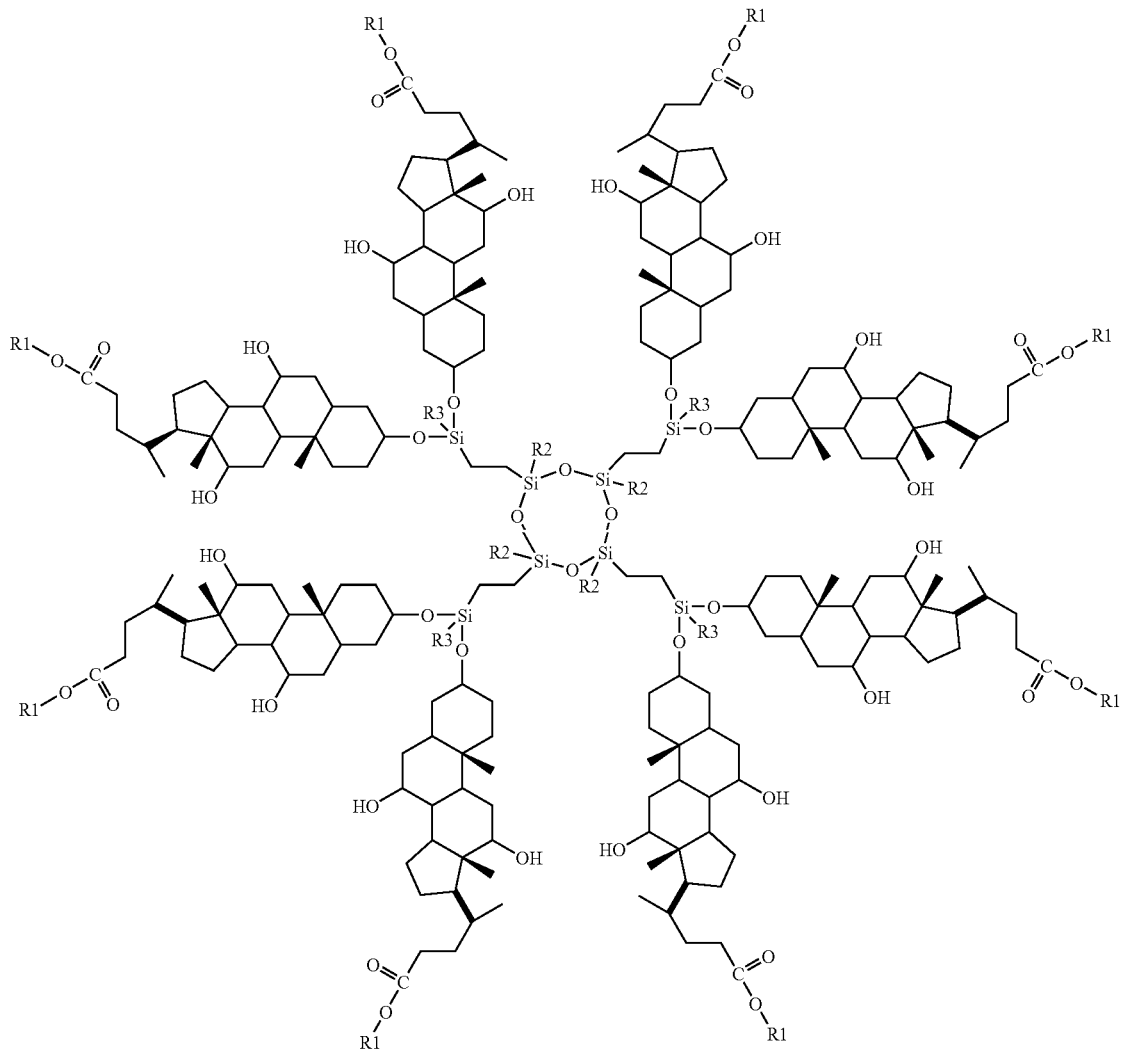

wherein R1 is a tertiary butyl group or a 1-(tert-butoxy)ethyl group, and each of R2 and R3 is, independently, a lower alkyl group having 1 to 4 carbon atoms.

Applying the photoresist composition to the mask layer may further include baking the photoresist composition and the mask layer at a temperature of about 110° C. to about 130° C. Partially exposing the photoresist film to the light may include employing a far ultraviolet ray, an argon fluoride (ArF) laser, a difluoride (F2) laser, an X-ray or an ion beam. Developing the photoresist film may include dissolving exposed portions of the photoresist film in a developing solution. Etching the mask layer may include oxygen plasma etching.

BRIEF DESCRIPTION OF THE DRAWINGS

The above and other features and advantages of the present invention will become more apparent to those of ordinary skill in the art by describing in detail example embodiments thereof with reference to the attached drawings, in which.

DETAILED DESCRIPTION OF THE INVENTION

Figure 1:
FIGS. 1-4 illustrate cross-sectional views of processing steps in a method of forming a photoresist pattern according to an example embodiment of the present invention.

Korean Patent Application No. 2005-128553 filed on Dec. 23, 2005, in the Korean Intellectual Property Office, is incorporated by reference herein in its entirety.

The present invention will now be described more fully hereinafter with reference to the accompanying drawings, in which example embodiments of the present invention are illustrated. The present invention may, however, be embodied in different forms and should not be construed as limited to the embodiments set forth herein. Rather, these embodiments are provided so that this disclosure will be thorough and complete, and will fully convey the scope of the invention to those skilled in the art.

In the figures, the dimensions of elements, layers, and regions may be exaggerated for clarity of illustration. It will also be understood that when an element or layer is referred to as being "on" another element, layer or substrate, it can be directly on the other layer or substrate, or intervening layers may also be present. Further, it will be understood that when an element is referred to as being "under" another element, it can be directly under, or one or more intervening elements may also be present. In addition, it will also be understood that when an element is referred to as being "between" two elements, it can be the only element between the two elements, or one or more intervening elements may also be present. Likewise, it will be understood that when an element or layer is referred to as being "connected to" or "coupled to" another element or layer, it can be directly connected to or coupled to the other element or layer, or intervening elements or layers may be present. In contrast, when an element is referred to as being "directly on," "directly connected to," or "directly coupled to" another element or layer, there may be no intervening elements or layers present. Like reference numerals and characters refer to like elements, compounds or layers throughout distinction As used herein, the term "and/or" may include any and all combinations of one or more of the associated listed items. As further used herein, the singular forms "a," "an" and "the" are intended to include the plural forms as well, unless the context clearly indicates otherwise.

Unless otherwise defined, all terminology used herein is given its ordinary meaning in the art, and therefore, should be interpreted within the context of the specification and the relevant art as understood by one of ordinary skill.

An example embodiment of a siloxane compound according to the present invention may include a single nonlinear molecule having a single molecular weight and a definite molecular structure, thereby reducing a molecular weight distribution and improving the photoresist pattern on a molecular level. In particular, the siloxane compound may include a protecting portion, an adhesion portion and an etching resistance portion.

The protecting portion of the siloxane compound may include a tertiary butyl group or a 1-(tert-butoxy) ethyl group, wherein a reaction between the protecting portion and an acid, e.g., an acid material generated from a PAG upon light irradiation, may separate the protecting portion from the siloxane compound. The adhesion portion may include a hydrophilic hydroxyl (OH) group. The etching resistance portion may include silicon (Si) atoms. The silicon atoms in the etching resistance portion may be transformed into silicon dioxide ($SiO_2$) during an oxygen plasma etching process, thereby improving the etching resistance of the siloxane compound.

In particular, the siloxane compound according to an embodiment of the present invention may have a chemical structure represented by formula (1):

Formula 1

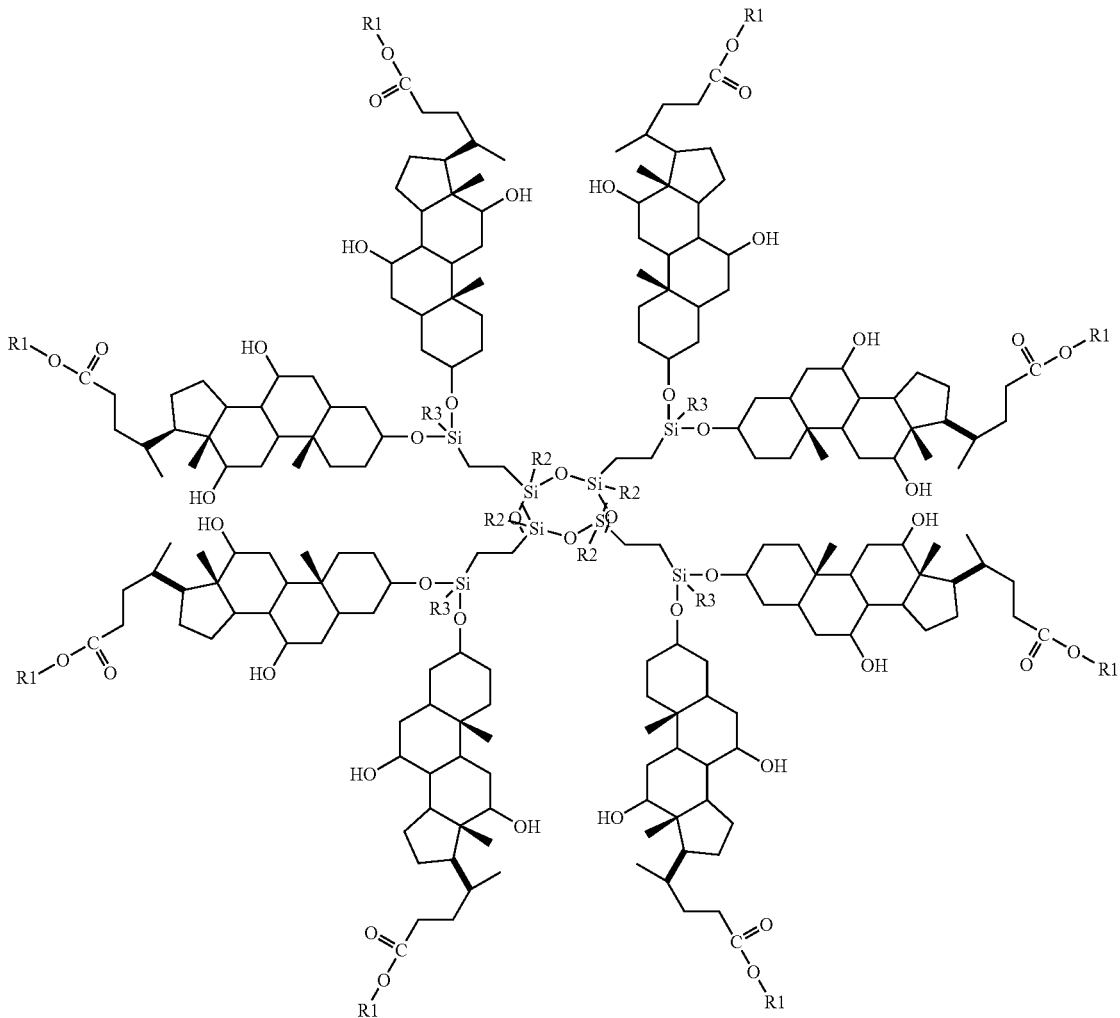

wherein R1 may represent a tertiary butyl group or a 1-(tert-butoxy)ethyl group acting as a protecting portion, and each of R2 and R3 may, independently, represent a lower alkyl group having 1 to 4 carbon atoms, e.g., a methyl group, an ethyl group, a propyl group or a butyl group.

The siloxane compound according to an example embodiment of the present invention may be synthesized by reacting a first reactant represented by formula (2) with a second reactant represented by formula (3). In this respect, it should be noted that descriptive terms such as "first," "second," and so forth may refer to compound or reactants employed in an embodiment of the present invention for the purpose of distinguishing one compound or reactant from another only.

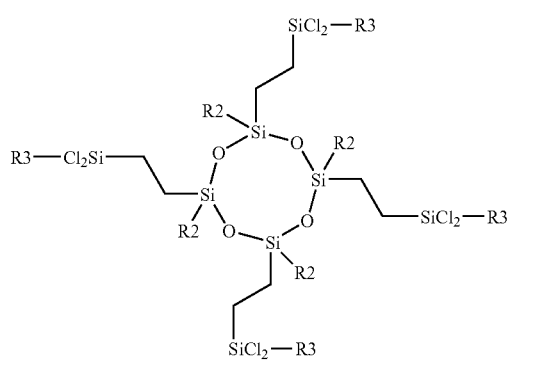

Formula 2

Formula 3

Alternatively, the siloxane compound may be synthesized by reacting the first reactant, i.e., the compound represented by formula (2), with a third reactant represented by formula (4) or with a fourth reactant represented by formula (5).

Formula 4

Formula 5

The first reactant, i.e., the compound represent by formula (2), may be synthesized by reacting a fifth reactant represented by formula (6) with dichloroalkylsilane ($Cl_2SiHR3$).

Formula 6

The siloxane compound according to an example embodiment of the present invention may have a flexible chain structure to increase amorphous characteristics thereof, i.e., provide a compound exhibiting more amorphous characteristics as opposed to crystalline characteristics. Accordingly and without intending to be bound by theory, it is believed that the siloxane compound of the present invention may be employed in a spin-coatable photoresist composition and, thereby, capable of providing a photoresist pattern having a reduced roughness pattern and an improved etching resistance upon application.

The siloxane compound according to an example embodiment of the present invention may further impart a large solubility difference between portions of the photoresist film that are exposed and unexposed to light irradiation due to the structure thereof, thereby increasing the uniformity of the formed photoresist pattern. Additionally, the structure of the siloxane compound, e.g., its relative small molecular size, short rotational radius and complex three-dimensional structure, may further reduce molecular interactions, e.g., chain entanglement, thereby further facilitating formation of a photoresist pattern having reduced pattern roughness and increased uniformity.

In another aspect of the present invention, an example embodiment of a photoresist composition employing the inventive siloxane compound will be described in detail below.

In particular, a photoresist composition in accordance with an example embodiment of the present invention may include a siloxane compound in an amount of from about 8% to about 14% by weight based on a total weight of the photoresist composition, a photoacid generator (PAG) in an amount of from about 0.1% to about 0.5% by weight based on a total weight of the photoresist composition, and a solvent. The siloxane compound of the inventive photoresist composition was previously described above, i.e., the siloxane compound represented by formula (1), and, therefore, a detailed description thereof will not be repeated herein.

When the amount of the siloxane compound in the photoresist composition is less than about 8% of the total weight of the photoresist composition, the photoresist composition may not be formed into a photoresist pattern. On the other hand, when the amount of the siloxane compound in the photoresist composition exceeds about 14% of the total weight of the photoresist composition, the photoresist pattern may have a non-uniform thickness, thereby increasing the pattern roughness thereof. Accordingly, for example, a photoresist composition employed for forming a photoresist pattern with a line width below about 80 nm may include the siloxane compound in an amount of about 9% to about 12% by weight based on a total weight of the photoresist composition.

The PAG of the photoresist composition may be employed to remove the protecting group of the siloxane compound. In particular, light may be irradiated onto the PAG to release an acid therefrom. The released acid may interact with the protecting group of the siloxane compound, such that the protecting group of the siloxane compound may be removed, thereby facilitating dissolution of the irradiated portions of the photoresist composition in a developing solution. Accordingly, the amount of acid (H$^+$) employed may be important for forming the photoresist pattern of the present invention.

When the amount of the PAG in the photoresist composition is less than about 0.1% by weight based on the total weight of the photoresist composition, an insufficient amount of acid (H$^+$) may be generated, thereby failing to properly separate the protecting group from the siloxane compound. On the other hand, when the amount of the PAG in the photoresist composition exceeds about 0.5% by weight based on the total weight of the photoresist composition, an excessive amount of acid (H$^+$) may be generated during light irradiation, thereby providing an excessively developed photoresist composition further requiring removal of an upper portion of the photoresist pattern.

The PAG of the photoresist composition may include a triarylsulfonium salt, a diaryliodonium salt, sulfonate, N-hydroxysuccinimide triflate, like compounds, or a combination thereof. More specifically, the PAG may include triphenylsulfonium triflate, triphenylsulfonium antimony salt, diphenyliodonium triflate, diphenyliodonium antimony salt, methoxydiphenyliodonium triflate, di-tert-butyldiphenyliodonium triflate, 2,6-dinitrobenzyl sulfonate, pyrogallol tris (alkylsufonate), norbornene-dicarboxyimide triflate, triphenylsulfonium nonaflate, diphenyliodonium nonaflate, methoxydiphenyliodonium nonaflate, di-tert-butyldiphenyliodonium nonaflate, N-hydroxysuccinimide nonaflate, norbornene dicarboxyimide nonaflate, triphenylsulfonium perfluoro-octanesulfonate, diphenyliodonium perfluoro-octanesulfonate, methoxyphenyliodonium perfluoro-octanesulfonate, di-tert- butyldiphenyliodonium triflate, N-hydroxysuccinimide perfluoro-octanesulfonate, norbornene dicarboxyimide perfluoro-octanesulfonate, or a combination thereof.

The solvent of the photoresist composition may include an organic compound such as ethylene glycol monomethyl ether, ethylene glycol monoethyl ether, propylene glycol methyl ether, methyl cellosolve acetate, ethyl cellosolve acetate, diethylene glycol monomethyl ether, diethylene glycol monoethyl ether, propylene glycol methyl ether acetate, propylene glycol propyl ether acetate, diethylene glycol dimethyl ether, ethyl lactate, toluene, xylene, methyl ethyl ketone, cyclohexanone, 2-heptanone, 3-heptanone, 4-heptanone, like solvents, or a combination thereof.

The photoresist composition according to an example embodiment of the present invention may further include an additive. In particular, the additive may include an organic base to facilitate shaping of the photoresist pattern and to minimize or reduce potential negative effects caused by external basic compounds, e.g., amine. For example, the additive may include an organic base, such as triethylamine, triisobutylamine, triisooctylamine, triisodecylamine, diethanolamine, triethanolamine, like organic bases, and combinations thereof.

In another aspect of the present invention, an example embodiment of a method of forming a photoresist pattern of a photoresist composition having the siloxane compound illustrated in formula 1 will be described in detail below with reference to FIGS. 1-4.

As illustrated in FIG. 1, a substrate 100, e.g., a silicon wafer, may be obtained and coated with a mask layer 102. The mask layer 102 may be formed, for example, by a spin coating process. The mask layer 102 may be formed of a material having physical properties such as enhanced gap filling capacity and planarization capability, high uniformity, good anti-reflection characteristics, great etching resistance, and so forth.

Next, the mask layer 102 may be cleaned to remove any potential contaminants from a surface thereof and may be coated with a photoresist composition to form a photoresist film 104 thereon. The photoresist composition employed to form the photoresist film 104 refers to the photoresist composition described above, i.e., the photoresist composition having the siloxane compound represented by formula (1), and, therefore, will not be described in detail herein. Once the photoresist film 104 is formed, the substrate 100 with the mask layer 102 and the photoresist film 104 thereon may be baked, i.e., a first baking process, at a temperature of about 90° C. to about 120° C. to improve adhesion between the photoresist film 104 and the mask layer 102.

Figure 2:
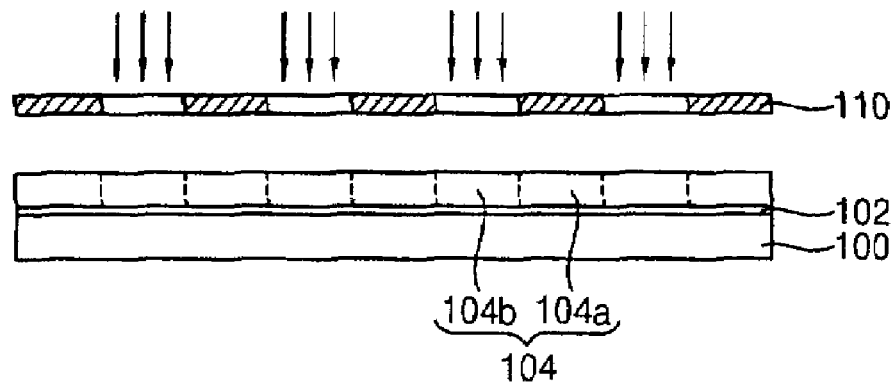

Subsequently, as illustrated in FIG. 2, the photoresist film 104 may be partially exposed to a light source, e.g., a far ultraviolet ray, an argon fluoride (ArF) laser, a difluoride (F2) laser, an X-ray, an ion beam, and so forth, through a mask 110. In particular, the mask 110 may include a pattern and may be positioned above the photoresist film 104, i.e., between the photoresist film 104 and the light source, such that light irradiated through the mask 110 may partially reach the photoresist film 104. In other words, the pattern in the mask 110 may selectively cover predetermined portions of the photoresist film 104, such that some uncovered portions of the photoresist film 104 may be irradiated, i.e., exposed portions 104b, while portions covered by the mask 110 may not be irradiated, i.e., unexposed portions 140a. The exposed portions 104b of the photoresist film 104 may be activated by the irradiating light, i.e., acid may be released from the PAG in response to the light irradiation to interact with the siloxane compound.

The exposed portions 104b of the photoresist film 104 may have higher hydrophilicity as compared to the unexposed portions 104a of the photoresist film 104, i.e., the exposed portions 104b may have higher solubility due to activation thereof. Accordingly, activation of the exposed portions 104b of the photoresist film 104 may be followed by heat treatment of the substrate with the mask layer 102 and the photoresist film 104 thereon, i.e., a second baking process, at a temperature of about 90° C. to about 150° C. to increase the solubility of the exposed portions 104b even further in a developing solution, e.g., tetramethylammonium hydroxide solution, thereby facilitating formation of a pattern corresponding to the pattern of the mask 110.

The exposed portions 104b may be removed from the substrate 100 by dissolving into the developing solution, i.e., developing the photoresist film 104, such that only the unexposed portions 104a may remain thereon. Without intending to be bound by theory, it is believed that the higher degree of hydrophilicity of the exposed portions 104b of the photoresist film 104 may provide substantially higher affinity between the exposed portion 104b and the developing solution as compared to the affinity between the unexposed portions 104a of the photoresist film 104 and the developing solution, thereby facilitating removal of the exposed portions 104b of the photoresist film 104 from the substrate 100.

Figure 3:
Figure 4:
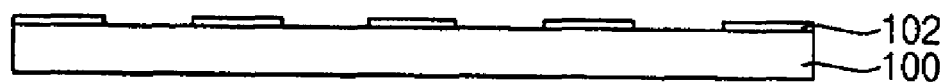

The exposed portions 104b may be removed from the substrate 100 by dissolving into the developing solution, i.e., the unexposed portions 104a may remain on the substrate 100. In particular, substrate 100 may undergo sequential cleaning and drying processes to complete a photoresist pattern 106 including the remaining unexposed portions 104a, as illustrated in FIG. 3. Accordingly, a photoresist pattern 106 may be formed in accordance with the pattern of the mask 110.

Next, the photoresist pattern 106 may be used as an etching mask to etch, e.g., remove portions by using oxygen plasma, the mask layer 102 and to form a pattern on the substrate 100, such that the pattern may correspond to the mask pattern 110.

Without intending to be bound by theory, it is believed that silicon atoms employed in the photoresist pattern 106 may be exposed to oxygen in the oxygen plasma etching, thereby forming silicon oxide ($SiO_2$) during the etching process. Formation of silicon dioxide in the photoresist pattern 106 may enhance an etching resistance thereof. In other words, the photoresist pattern 106 may remain on the substrate 100 during the entire etching process, i.e., until formation of the mask pattern 110 on the substrate 100 is complete, thereby preventing or reducing defective semiconductor patterning due to premature removal and/or dissolution of a photoresist pattern during etching.

EXAMPLES

Example 1

Synthesis of the Siloxane Compound: A three-neck flask having a volume of 250 ml was connected to a dry tube filled up with anhydrous calcium chloride ($CaCl_2$), and nitrogen ($N_2$) gas was charged into the three-neck flask. Next, 3.72 g, i.e., 0.008 mol, of tert-butyl cholate (TBC) and 0.81 g, i.e., 0.008 mol, of tetraethyl ammonium (TEA) were dissolved in 20 ml of an anhydrous tetrahydrofuran (THF) solution in the three-neck flask to form a first mixture. Then, the first mixture was agitated until its temperature was reduced to 0° C., and 0.46 g, i.e., 0.001 mol, of 2,4,6,8-tetramethyl-2,4,6,8-tetra (dichloromethylsilyl) ethylcyclotetrasiloxane dissolved in 10ml of an anhydrous tetrahydrofuran (THF) solution was slowly introduced into the first mixture through a dropping funnel to form a second mixture. Subsequently, a temperature of the second mixture was increased to a room temperature and was maintained for six hours to allow reaction between the first mixture and the 2,4,6,8-tetramethyl-2,4,6,8-tetra (dichloromethylsilyl)ethylcyclotetrasiloxane.

Next, a solvent of the second mixture was evaporated using a TEA salt as a filter to obtain a residue. Then, the residue was washed with 300 ml of diethyl ether and 200 ml of saturated aqueous $NaHCO_3$ solution to form an organic residue. The organic residue was washed with 200 ml of pure water, followed by a dehydration process using anhydrous $MgSO_4$. Then, the $MgSO_4$ was removed from the resultant of the hydration process and the solvent was evaporated. A final product, i.e., siloxane compound, was separated from the resultant by a column chromatography.

A chemical structure of the siloxane product was confirmed using a $^1$H-nuclear magnetic resonance ($^1$H-NMR) spectrum, a $^{29}$Si-NMR spectrum and an FT-IR spectrum. The $^1$H-NMR spectrum was obtained using the final product dissolved in chloroform-d ($CDCl_3$). The $^1$H-NMR spectrum showed chemical shifts (δ) of the final product at 0.05 ppm (36H, s, $CH_3Si$—), 0.65 ppm (3H, s, 18-methyl), 0.88 ppm (3H, s, 19-methyl), 0.96 ppm (3H, d, J=6 Hz, 21-methyl), 1.01-2.02 ppm (26H, m), 1.41 ppm (9H, s, t-butyl), 3.86 ppm (1H, m) and 3.96 ppm (1H, m). The $^{29}$Si-NMR spectrum was obtained using the final product dissolved in chloroform-d ($CDCl_3$). The $^{29}$Si-NMR spectrum showed chemical shifts (δ) of the final product at −18.1 ppm and −32.6 ppm. The FT-IR spectrum showed peaks at 2940 $cm^{-1}$ (aliphatic and alicyclic CH) and 1729 $cm^{-1}$ (C=O of ester). From the analysis of the $^1$H-NMR spectrum, the $^{29}$Si-NMR spectrum and the FT-IR spectrum, it was confirmed that the final product was 2,4,6,8-Tetra(diTBCsilyl)ethyl-2,4,6,8- tetramethylcyclo-siloxane having a chemical structure represented by formula (7).

Formula 7

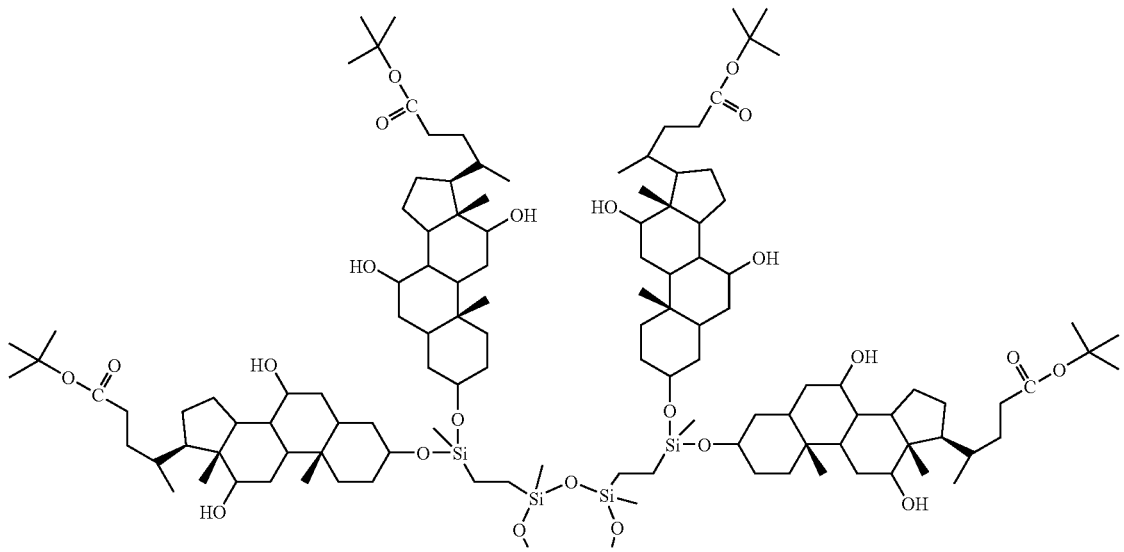

-continued

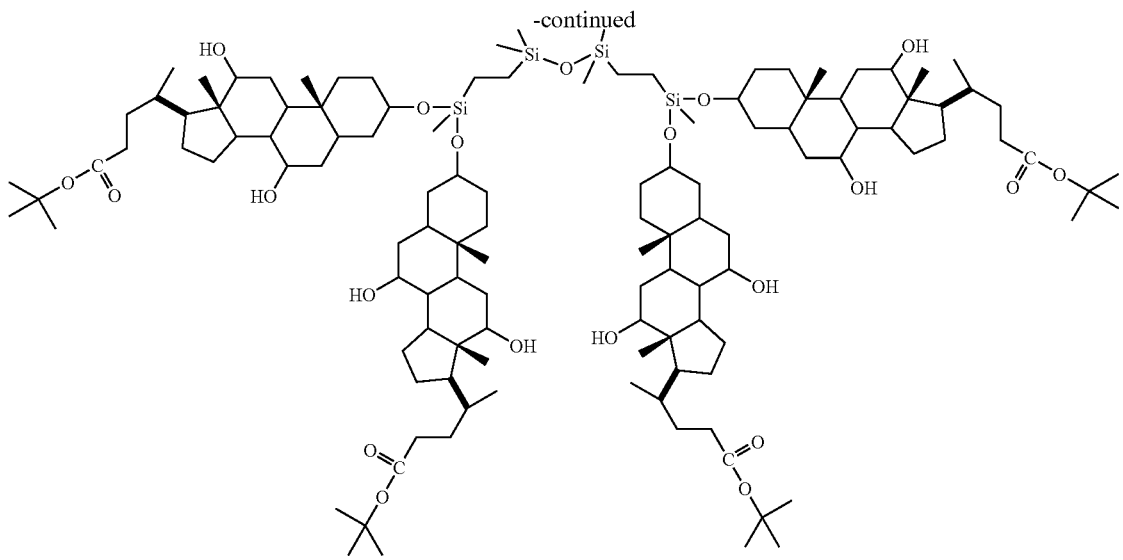

Example 2

Preparation of a Photoresist Composition: A photoresist composition was prepared by mixing 1 g, i.e., 10% by weight, of the siloxane compound synthesized in Example 1, 0.02 g, i.e., 0.2% be weight, of triphenylsulfonium triflate as a photoacid generator, and 8.98 g, i.e., 89.8% by weight, of propylene glycol methyl ether as an organic solvent.

Example 3

Formation of a Photoresist Pattern: An organic mask layer was formed on a substrate and coated with the photoresist composition prepared in Example 2. The substrate with the organic mask layer and the photoresist composition thereon was heat treated to form a first photoresist film having a thickness of 3,000 angstroms. Next, the first photoresist film was partially, i.e., through a mask, exposed to an Hg—Xe laser and heat treated at a temperature of 110° C. for about 90 seconds.

Consequently, exposed portions of the first photoresist film were dissolved into a developing solution of tetramethylammonium hydroxide (TMAH). The substrate with the organic mask layer and the remaining portions of the photoresist film was cleaned and dried to remove any remains of the developing solution to complete formation of a first photoresist pattern on the organic mask layer.

Then, the organic mask layer was partially etched by oxygen plasma etching using the first photoresist pattern as an etching mask to form a mask pattern on the substrate. The oxygen gas was provided at a flow rate of 30 sccm, and the etching process was performed under the conditions of RF power of 100 W and pressure of 200 mTorr.

Example 4

Comparison of the Inventive Photoresist Pattern to Conventional Art: a comparative photoresist composition was prepared by mixing 11.1% by weight of a compound having no silicon atoms, which was prepared by reacting 1,3,5-cyclohexanetricarboxylic acid with tert-butyl cholate, 0.2% by weight of triphenylsulfonium triflate as a photoacid generator, and 88.7% by weight of propylene glycol methyl ether as an organic solvent.

Next, a comparative photoresist pattern was prepared by forming an organic mask layer on a substrate and coating the organic mask layer with the comparative photoresist composition. The remaining procedure was identical to the procedure described in Example 3, thereby forming a comparative photoresist pattern. Then, the organic mask layer was partially etched by oxygen plasma etching using the comparative photoresist pattern as an etching mask to form a mask pattern on the substrate. The etching conditions were similar to the etching conditions in Example 3.

A relative amount of each photoresist pattern, i.e., the first photoresist pattern and the comparative photoresist pattern, lost in the plasma etching process was evaluated. Evaluation results of Example 4 are provided in Table 1.

TABLE 1

| | Lost Amount of a Photoresist Pattern |
|---|---|
| First Photoresist Pattern | Small |
| Comparative Photoresist Pattern | Large |

The photoresist composition and pattern according to the present invention may be advantageous because they include a siloxane compound having silicon atoms, thereby enhancing the etching resistance of the photoresist pattern during oxygen plasma etching process. Accordingly, the inventive photoresist pattern may provide an improved photolithography mask and enhance the overall quality and efficiency of semiconductor manufacturing.

Example embodiments of the present invention have been disclosed herein, and although specific terms are employed, they are used and are to be interpreted in a generic and descriptive sense only and not for purpose of limitation. Accordingly, it will be understood by those of ordinary skill in the art that various changes in form and details may be made without departing from the spirit and scope of the present invention as set forth in the following claims.

What is claimed is:

1. A siloxane compound represented by Formula (1):

Formula 1

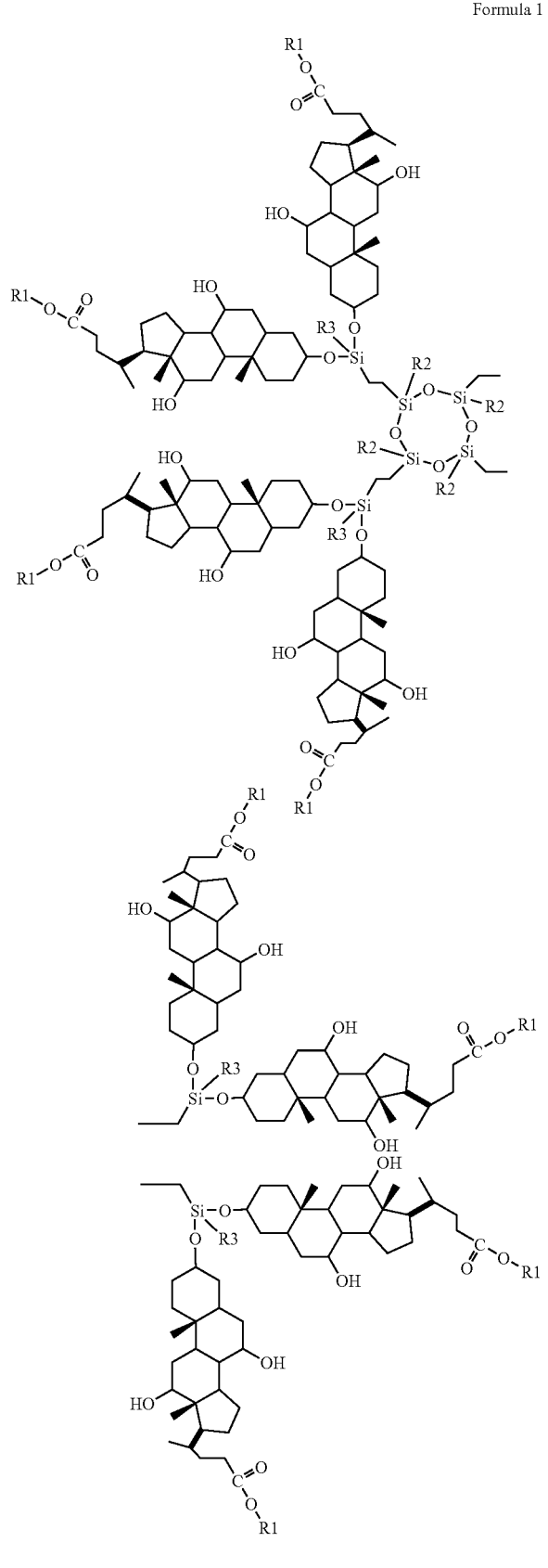

wherein R1 is a tertiary butyl group or a 1-(tert-butoxy)ethyl group, and each of R2 and R3 is, independently, a lower alkyl group having 1 to 4 carbon atoms.

2. The siloxane compound as claimed in claim 1, wherein the siloxane compound is a product of a chemical reaction between a first reactant represented by Formula (2) and a second reactant represented by Formula (3):

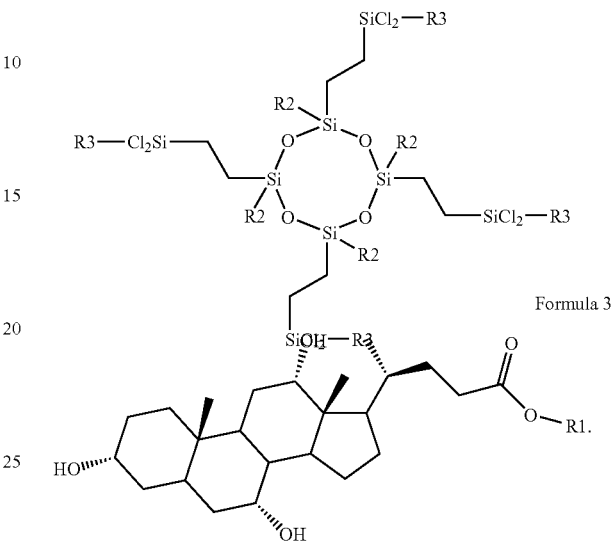

3. A photoresist composition comprising a siloxane compound in an amount of about 8 to about 14 percent by weight of the photoresist composition, a photoacid generator in an amount of about 0.1 to about 0.5 percent by weight of the photoresist composition, and an organic solvent, wherein the siloxane compound is represented by Formula (1):

Formula 1

-continued

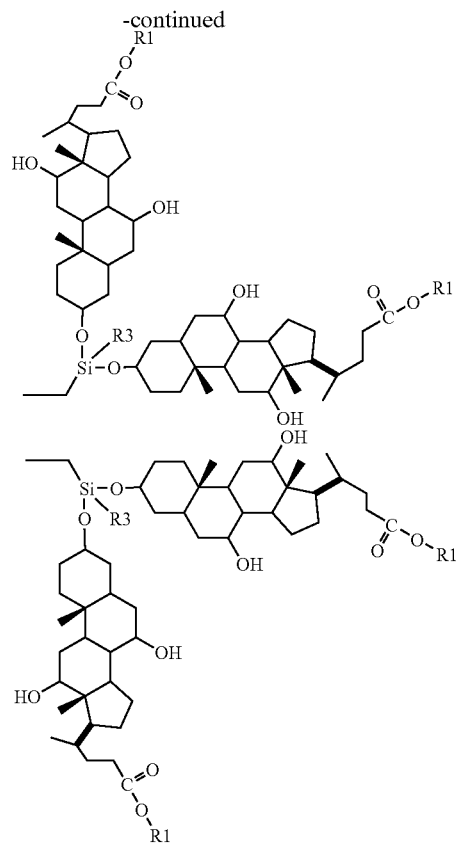

wherein R1 is a tertiary butyl group or a 1-(tert-butoxy)ethyl group, and each of R2 and R3 is, independently, a lower alkyl group having 1 to 4 carbon atoms.

4. The photoresist composition as claimed in claim 3, wherein the photoacid generator is triarylsulfonium salt, diaryliodonium salt, sulfonate, N-hydroxysuccinimide triflate or a combination thereof.

5. The photoresist composition as claimed in claim 3, wherein the organic solvent is ethylene glycol monomethyl ether, ethylene glycol monoethyl ether, propylene glycol methyl ether, methyl cellosolve acetate, ethyl cellosolve acetate, diethylene glycol monomethyl ether, diethylene glycol monoethyl ether, propylene glycol methyl ether acetate, propylene glycol propylether acetate, diethylene glycol dimethylether, ethyl lactate, toluene, xylene, methyl ethyl ketone, cyclohexanone, 2-heptanone, 3-heptanone, 4-heptanone or a combination thereof.

6. A method of forming a pattern on a substrate, comprising:
   coating the substrate with a mask layer;
   preparing a photoresist composition having about 8 to about 14 percent by weight of a siloxane compound, about 0.1 to about 0.5 percent by weight of a photoacid generator, and an organic solvent;
   applying the photoresist composition to the mask layer to form a photoresist film;
   partially exposing the photoresist film to a light;
   developing the photoresist film into a photoresist pattern; and
   etching the mask layer through the photoresist pattern to form the pattern on the substrate;

wherein the siloxane compound is represented by Formula (1):

Formula 1

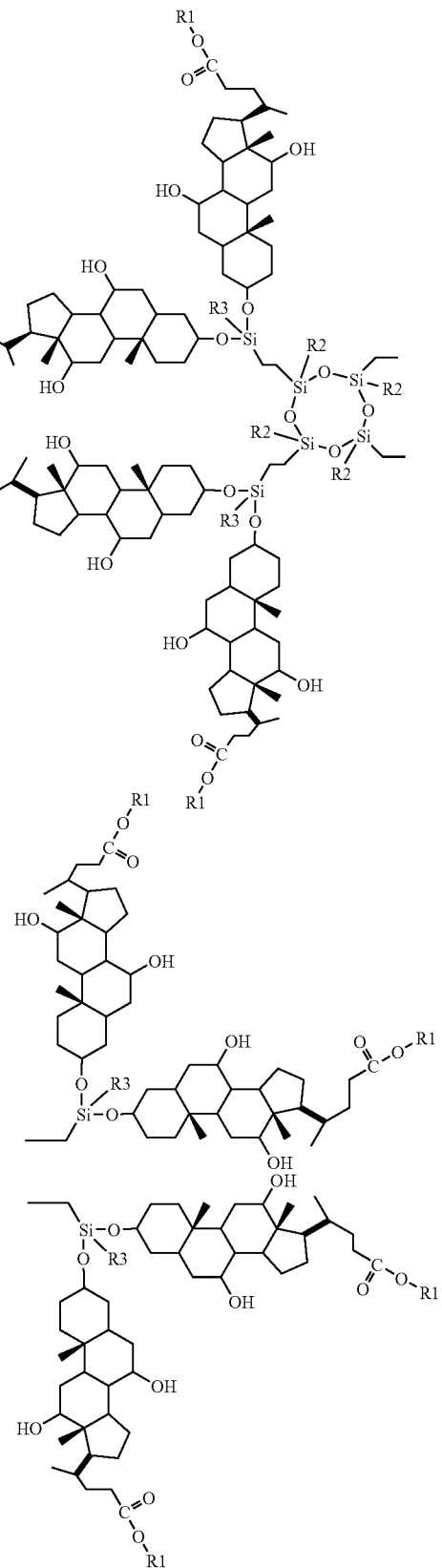

wherein R1 is a tertiary butyl group or a 1-(tert-butoxy)ethyl group, and each of R2 and R3 is, independently, a lower alkyl group having 1 to 4 carbon atoms.

7. The method as claimed in claim 6, after applying the photoresist composition to the mask layer, further comprising baking the photoresist film at a temperature of about 110° C. to about 130° C.

8. The method as claimed in claim 6, wherein partially exposing the photoresist film to light includes employing a far ultraviolet ray, an argon fluoride (ArF) laser, a difluoride (F2) laser, an X-ray or an ion beam.

9. The method as claimed in claim 6, wherein developing the photoresist film includes dissolving exposed portions of the photoresist film in a developing solution.

10. The method as claimed in claim 6, wherein etching the mask layer includes oxygen plasma etching.

* * * * *